United States Patent
Duffield et al.

(10) Patent No.: US 9,615,936 B2
(45) Date of Patent: Apr. 11, 2017

(54) INTERVERTEBRAL FUSION IMPLANT

(71) Applicant: GLOBUS MEDICAL, INC., Audubon, PA (US)

(72) Inventors: William E. Duffield, Collegeville, PA (US); Colm McLaughlin, Glenside, PA (US); Jason Gray, East Greenville, PA (US); Jamie Carroll, Drexel Hill, PA (US); Mark Adams, Downington, PA (US); William S. Rhoda, Media, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 14/209,504

(22) Filed: Mar. 13, 2014

(65) Prior Publication Data

US 2014/0194994 A1    Jul. 10, 2014

Related U.S. Application Data

(63) Continuation of application No. 12/477,958, filed on Jun. 4, 2009, now Pat. No. 8,709,083.

(51) Int. Cl.
*A61F 2/44* (2006.01)
*A61F 2/30* (2006.01)
(Continued)

(52) U.S. Cl.
CPC ............ *A61F 2/4455* (2013.01); *A61F 2/447* (2013.01); *A61F 2/30734* (2013.01);
(Continued)

(58) Field of Classification Search
CPC ........... A61F 2/44; A61F 2/4455; A61F 2/447
See application file for complete search history.

(56) References Cited

U.S. PATENT DOCUMENTS

| | | | |
|---|---|---|---|
| 1,673,630 A | 6/1928 | Madge | |
| 4,349,921 A | 9/1982 | Kuntz | |
| (Continued) | | | |

FOREIGN PATENT DOCUMENTS

| | | | |
|---|---|---|---|
| FR | 2727003 A1 | 5/1996 | |
| WO | 9723175 A1 | 7/1997 | |
| (Continued) | | | |

OTHER PUBLICATIONS

U.S. Appl. No. 60/777,663, Feb. 27, 2006, Messerli.
(Continued)

*Primary Examiner* — Nicholas Woodall

(57) ABSTRACT

The present invention provides an intervertebral implant for implantation in a treated area of an intervertebral space between vertebral bodies of a spine. The implant includes a spacer portion having an inferior and superior surface, wherein the inferior and superior surfaces each have a contact area capable of engaging with anatomy in the treated area, and the inferior and superior surfaces define a through-hole extending through the spacer body. The present invention further provides screw holes extending from a side portion to the inferior and superior surfaces of the spacer portion and a plate portion coupled to the spacer portion through a coupling means, wherein the plate portion contains screws holes for receiving screws. A screw back out prevention mechanism adapted on the plate portion and prevents the back out of screws from the screw holes.

15 Claims, 6 Drawing Sheets

(51) Int. Cl.
  *A61F 2/46* (2006.01)
  *A61F 2/28* (2006.01)
(52) U.S. Cl.
  CPC ..... *A61F 2/4684* (2013.01); *A61F 2002/2835* (2013.01); *A61F 2002/3082* (2013.01); *A61F 2002/30403* (2013.01); *A61F 2002/30433* (2013.01); *A61F 2002/30436* (2013.01); *A61F 2002/30492* (2013.01); *A61F 2002/30509* (2013.01); *A61F 2002/30517* (2013.01); *A61F 2002/30578* (2013.01); *A61F 2002/30616* (2013.01); *A61F 2002/30787* (2013.01); *A61F 2002/30794* (2013.01); *A61F 2002/30843* (2013.01); *A61F 2002/30904* (2013.01); *A61F 2002/4475* (2013.01); *A61F 2310/00023* (2013.01)

(56) References Cited

U.S. PATENT DOCUMENTS

| | | |
|---|---|---|
| 4,599,086 A | 7/1986 | Doty |
| 4,743,256 A | 5/1988 | Brantigan |
| 4,834,757 A | 5/1989 | Brantigan |
| 4,904,261 A | 2/1990 | Dove et al. |
| 4,917,704 A | 4/1990 | Frey |
| 4,955,908 A | 9/1990 | Frey |
| 5,002,576 A | 3/1991 | Fuhrmann et al. |
| 5,163,949 A | 11/1992 | Bonutti |
| 5,163,960 A | 11/1992 | Bonutti |
| 5,197,971 A | 3/1993 | Bonutti |
| 5,269,785 A | 12/1993 | Bonutti |
| 5,295,994 A | 3/1994 | Bonutti |
| 5,329,846 A | 7/1994 | Bonutti |
| 5,331,975 A | 7/1994 | Bonutti |
| 5,345,927 A | 9/1994 | Bonutti |
| 5,364,399 A | 11/1994 | Lowery et al. |
| 5,397,364 A | 3/1995 | Kozak et al. |
| 5,403,317 A | 4/1995 | Bonutti |
| 5,403,348 A | 4/1995 | Bonutti |
| 5,441,538 A | 8/1995 | Bonutti |
| 5,454,365 A | 10/1995 | Bonutti |
| 5,458,641 A | 10/1995 | Jiminez |
| 5,464,426 A | 11/1995 | Bonutti |
| 5,496,348 A | 3/1996 | Bonutti |
| 5,514,153 A | 5/1996 | Bonutti |
| 5,514,180 A | 5/1996 | Heggeness |
| 5,522,846 A | 6/1996 | Bonutti |
| 5,527,343 A | 6/1996 | Bonutti |
| 5,534,012 A | 7/1996 | Bonutti |
| 5,545,222 A | 8/1996 | Bonutti |
| 5,549,612 A | 8/1996 | Yapp et al. |
| 5,549,630 A | 8/1996 | Bonutti |
| 5,549,631 A | 8/1996 | Bonutti |
| 5,569,305 A | 10/1996 | Bonutti |
| 5,577,517 A | 11/1996 | Bonutti |
| 5,584,862 A | 12/1996 | Bonutti |
| 5,593,425 A | 1/1997 | Bonutti |
| 5,624,462 A | 4/1997 | Bonutti |
| 5,645,596 A | 7/1997 | Kim et al. |
| 5,662,710 A | 9/1997 | Bonutti |
| 5,667,520 A | 9/1997 | Bonutti |
| 5,685,826 A | 11/1997 | Bonutti |
| 5,694,951 A | 12/1997 | Bonutti |
| 5,707,390 A | 1/1998 | Bonutti |
| 5,716,325 A | 2/1998 | Bonutti |
| 5,733,306 A | 3/1998 | Bonutti |
| 5,735,875 A | 4/1998 | Bonutti |
| 5,827,318 A | 10/1998 | Bonutti |
| 5,845,645 A | 12/1998 | Bonutti |
| 5,860,997 A | 1/1999 | Bonutti |
| 5,861,041 A | 1/1999 | Tienboon |
| 5,888,196 A | 3/1999 | Bonutti |
| 5,888,219 A | 3/1999 | Bonutti |
| 5,888,223 A | 3/1999 | Bray, Jr. |
| 5,928,267 A | 7/1999 | Bonutti |
| 5,935,131 A | 8/1999 | Bonutti |
| 5,941,900 A | 8/1999 | Bonutti |
| 5,954,739 A | 9/1999 | Bonutti |
| 6,010,525 A | 1/2000 | Bonutti |
| 6,017,305 A | 1/2000 | Bonutti |
| 6,042,596 A | 3/2000 | Bonutti |
| 6,045,579 A | 4/2000 | Hochshuler |
| 6,059,817 A | 5/2000 | Bonutti |
| 6,066,175 A | 5/2000 | Henderson et al. |
| 6,077,292 A | 6/2000 | Bonutti |
| 6,086,593 A | 7/2000 | Bonutti |
| 6,099,531 A | 8/2000 | Bonutti |
| 6,102,928 A | 8/2000 | Bonutti |
| 6,132,472 A | 10/2000 | Bonutti |
| RE36,974 E | 11/2000 | Bonutti |
| 6,146,421 A | 11/2000 | Gordon |
| 6,156,037 A | 12/2000 | LeHuec et al. |
| 6,159,234 A | 12/2000 | Bonutti |
| 6,171,236 B1 | 1/2001 | Bonutti |
| 6,171,299 B1 | 1/2001 | Bonutti |
| 6,174,313 B1 | 1/2001 | Bonutti |
| 6,187,023 B1 | 2/2001 | Bonutti |
| 6,200,347 B1 | 3/2001 | Anderson et al. |
| 6,203,565 B1 | 3/2001 | Bonutti |
| 6,206,922 B1 | 3/2001 | Zdeblick et al. |
| 6,217,617 B1 | 4/2001 | Bonutti |
| 6,231,592 B1 | 5/2001 | Bonutti |
| 6,231,610 B1 | 5/2001 | Geisler |
| 6,235,059 B1 | 5/2001 | Benezech |
| 6,258,089 B1 | 7/2001 | Campbell et al. |
| 6,277,136 B1 | 8/2001 | Bonutti |
| 6,287,325 B1 | 9/2001 | Bonutti |
| 6,342,074 B1 | 1/2002 | Simpson |
| 6,358,266 B1 | 3/2002 | Bonutti |
| 6,361,565 B1 | 3/2002 | Bonutti |
| 6,364,880 B1 | 4/2002 | Michelson |
| 6,368,343 B1 | 4/2002 | Bonutti |
| 6,383,186 B1 | 5/2002 | Michelson |
| 6,425,920 B1 | 7/2002 | Hamada |
| 6,432,106 B1 | 8/2002 | Fraser |
| 6,447,516 B1 | 9/2002 | Bonutti |
| 6,451,042 B1 | 9/2002 | Bonutti |
| 6,464,713 B2 | 10/2002 | Bonutti |
| 6,468,289 B1 | 10/2002 | Bonutti |
| 6,468,293 B2 | 10/2002 | Bonutti |
| 6,471,724 B2 | 10/2002 | Zdeblick |
| 6,475,230 B1 | 11/2002 | Bonutti |
| 6,482,233 B1 * | 11/2002 | Aebi et al. ................. 623/17.11 |
| 6,500,195 B2 | 12/2002 | Bonutti |
| 6,503,267 B2 | 1/2003 | Bonutti |
| 6,503,277 B2 | 1/2003 | Bonutti |
| 6,520,993 B2 | 2/2003 | James |
| 6,540,785 B1 | 4/2003 | Gill et al. |
| 6,543,455 B2 | 4/2003 | Bonutti |
| 6,558,387 B2 | 5/2003 | Errico |
| 6,558,423 B1 | 5/2003 | Michelson |
| 6,558,424 B2 | 5/2003 | Thalgott |
| 6,562,073 B2 | 5/2003 | Foley |
| 6,569,187 B1 | 5/2003 | Bonutti |
| 6,575,982 B1 | 6/2003 | Bonutti |
| 6,585,750 B2 | 7/2003 | Bonutti |
| 6,592,531 B2 | 7/2003 | Bonutti |
| 6,592,609 B1 | 7/2003 | Bonutti |
| 6,607,534 B2 | 8/2003 | Bonutti |
| 6,620,181 B1 | 9/2003 | Bonutti |
| 6,629,998 B1 | 10/2003 | Lin |
| 6,630,000 B1 | 10/2003 | Bonutti |
| 6,635,073 B2 | 10/2003 | Bonutti |
| 6,638,309 B2 | 10/2003 | Bonutti |
| 6,652,532 B2 | 11/2003 | Bonutti |
| 6,666,889 B1 | 12/2003 | Commarmond |
| 6,682,563 B2 | 1/2004 | Scharf |
| 6,702,821 B2 | 3/2004 | Bonutti |
| 6,702,856 B2 | 3/2004 | Bonutti |
| 6,709,458 B2 | 3/2004 | Michelson |
| 6,719,803 B2 | 4/2004 | Bonutti |
| 6,730,127 B2 * | 5/2004 | Michelson ................. 623/17.16 |
| 6,736,853 B2 | 5/2004 | Bonutti |

(56) References Cited

U.S. PATENT DOCUMENTS

| | | |
|---|---|---|
| 6,740,118 B2 | 5/2004 | Eisermann et al. |
| 6,770,078 B2 | 8/2004 | Bonutti |
| 6,776,938 B2 | 8/2004 | Bonutti |
| 6,793,658 B2 | 9/2004 | Lehuec |
| 6,805,714 B2 | 10/2004 | Sutcliffe |
| 6,827,740 B1 | 12/2004 | Michelson |
| 6,835,198 B2 | 12/2004 | Bonutti |
| 6,835,206 B2 | 12/2004 | Jackson |
| 6,849,093 B2 | 2/2005 | Michelson |
| 6,860,885 B2 | 3/2005 | Bonutti |
| 6,860,904 B2 | 3/2005 | Bonutti |
| 6,887,272 B2 | 5/2005 | Shinomiya |
| 6,899,735 B2 | 5/2005 | Coates et al. |
| 6,905,517 B2 | 6/2005 | Bonutti |
| 6,908,466 B1 | 6/2005 | Bonutti |
| 6,932,835 B2 | 8/2005 | Bonutti |
| 6,972,019 B2 | 12/2005 | Michelson |
| 6,989,029 B2 | 1/2006 | Bonutti |
| 6,990,982 B1 | 1/2006 | Bonutti |
| 7,001,432 B2 | 2/2006 | Keller et al. |
| 7,025,787 B2 | 4/2006 | Bryan et al. |
| 7,044,972 B2 | 5/2006 | Mathys, Jr. |
| 7,048,755 B2 | 5/2006 | Bonutti |
| 7,070,557 B2 | 7/2006 | Bonutti |
| 7,087,073 B2 | 8/2006 | Bonutti |
| 7,094,251 B2 | 8/2006 | Bonutti |
| 7,104,996 B2 | 9/2006 | Bonutti |
| 7,114,500 B2 | 10/2006 | Bonutti |
| 7,128,753 B1 | 10/2006 | Bonutti |
| 7,134,437 B2 | 11/2006 | Bonutti |
| 7,137,997 B2 | 11/2006 | Paul |
| 7,147,652 B2 | 12/2006 | Bonutti |
| 7,147,665 B1 | 12/2006 | Bryan et al. |
| 7,153,325 B2 | 12/2006 | Kim et al. |
| 7,163,561 B2 | 1/2007 | Michelson |
| 7,172,627 B2 | 2/2007 | Fiere et al. |
| 7,192,447 B2 | 3/2007 | Rhoda |
| 7,208,013 B1 | 4/2007 | Bonutti |
| 7,217,273 B2 | 5/2007 | Bonutti |
| 7,217,290 B2 | 5/2007 | Bonutti |
| 7,232,464 B2 | 6/2007 | Mathieu et al. |
| 7,238,203 B2 | 7/2007 | Bagga et al. |
| 7,276,082 B2 | 10/2007 | Zdeblick et al. |
| 7,309,357 B2 | 12/2007 | Kim |
| 7,311,719 B2 | 12/2007 | Bonutti |
| 7,320,708 B1 | 1/2008 | Bernstein |
| 7,323,011 B2 * | 1/2008 | Shepard et al. ........... 623/17.11 |
| 7,329,263 B2 | 2/2008 | Bonutti |
| 7,429,266 B2 | 9/2008 | Bonutti |
| 7,462,200 B2 | 12/2008 | Bonutti |
| 7,481,831 B2 | 1/2009 | Bonutti |
| 7,510,557 B1 | 3/2009 | Bonutti |
| 7,594,931 B2 | 9/2009 | Louis et al. |
| 7,615,054 B1 | 11/2009 | Bonutti |
| 7,618,456 B2 | 11/2009 | Mathieu et al. |
| 7,635,390 B1 | 12/2009 | Bonutti |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,771,475 B2 | 8/2010 | Michelson |
| 7,780,670 B2 | 8/2010 | Bonutti |
| 7,794,502 B2 | 9/2010 | Michelson |
| 7,806,896 B1 | 10/2010 | Bonutti |
| 7,806,897 B1 | 10/2010 | Bonutti |
| 7,828,852 B2 | 11/2010 | Bonutti |
| 7,837,736 B2 | 11/2010 | Bonutti |
| 7,846,207 B2 | 12/2010 | Lechmann et al. |
| 7,850,731 B2 | 12/2010 | Brittain |
| 7,854,750 B2 | 12/2010 | Bonutti |
| 7,862,616 B2 | 1/2011 | Lechmann et al. |
| 7,875,076 B2 | 1/2011 | Mathieu et al. |
| 7,879,072 B2 | 2/2011 | Bonutti |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,959,635 B1 | 6/2011 | Bonutti |
| 7,972,381 B2 | 7/2011 | Michelson |
| 8,100,976 B2 | 1/2012 | Bray et al. |
| 8,105,383 B2 | 1/2012 | Michelson |
| 8,114,162 B1 | 2/2012 | Bradley |
| 8,128,669 B2 | 3/2012 | Bonutti |
| 8,133,229 B1 | 3/2012 | Bonutti |
| 8,137,405 B2 | 3/2012 | Kostuik et al. |
| 8,162,977 B2 | 4/2012 | Bonutti |
| 8,216,312 B2 | 7/2012 | Gray |
| 8,268,000 B2 | 9/2012 | Waugh et al. |
| 8,323,343 B2 | 12/2012 | Michelson |
| 8,328,872 B2 | 12/2012 | Duffield et al. |
| 8,343,222 B2 | 1/2013 | Cope |
| 8,425,522 B2 | 4/2013 | Bonutti |
| 8,425,607 B2 | 4/2013 | Waugh et al. |
| 8,439,977 B2 | 5/2013 | Kostuik et al. |
| 8,486,066 B2 | 7/2013 | Bonutti |
| 8,623,030 B2 | 1/2014 | Bonutti |
| 8,632,552 B2 | 1/2014 | Bonutti |
| 8,641,726 B2 | 2/2014 | Bonutti |
| 8,690,944 B2 | 4/2014 | Bonutti |
| 8,739,797 B2 | 6/2014 | Bonutti |
| 8,747,439 B2 | 6/2014 | Bonutti |
| 8,784,495 B2 | 7/2014 | Bonutti |
| 8,795,363 B2 | 8/2014 | Bonutti |
| 8,814,902 B2 | 8/2014 | Bonutti |
| 8,834,490 B2 | 9/2014 | Bonutti |
| 8,840,629 B2 | 9/2014 | Bonutti |
| 8,845,699 B2 | 9/2014 | Bonutti |
| 8,858,557 B2 | 10/2014 | Bonutti |
| 8,956,417 B2 | 2/2015 | Bonutti |
| 9,044,322 B2 | 6/2015 | Bonutti |
| 9,044,341 B2 | 6/2015 | Bonutti |
| 9,050,152 B2 | 6/2015 | Bonutti |
| 2001/0005796 A1 | 6/2001 | Zdeblick |
| 2001/0023371 A1 | 9/2001 | Bonutti |
| 2001/0034553 A1 | 10/2001 | Michelson |
| 2002/0004683 A1 | 1/2002 | Michelson |
| 2002/0010511 A1 | 1/2002 | Michelson |
| 2002/0016595 A1 | 2/2002 | Michelson |
| 2002/0029055 A1 | 3/2002 | Bonutti |
| 2002/0040246 A1 | 4/2002 | Bonutti |
| 2002/0082597 A1 | 6/2002 | Fraser |
| 2002/0095160 A1 | 7/2002 | Bonutti |
| 2002/0138146 A1 | 9/2002 | Jackson |
| 2002/0143399 A1 | 10/2002 | Sutcliffe |
| 2002/0147450 A1 | 10/2002 | Lehuec |
| 2003/0009147 A1 | 1/2003 | Bonutti |
| 2003/0023260 A1 | 1/2003 | Bonutti |
| 2003/0045939 A1 | 3/2003 | Casutt |
| 2003/0105528 A1 | 6/2003 | Shimp et al. |
| 2003/0125739 A1 | 7/2003 | Bagga et al. |
| 2003/0167091 A1 | 9/2003 | Scharf |
| 2003/0181981 A1 | 9/2003 | Lemaire |
| 2004/0010287 A1 | 1/2004 | Bonutti |
| 2004/0078078 A1 | 4/2004 | Shepard |
| 2004/0082998 A1 | 4/2004 | Shinomiya |
| 2004/0082999 A1 | 4/2004 | Robert, Jr. |
| 2004/0097794 A1 | 5/2004 | Bonutti |
| 2004/0098016 A1 | 5/2004 | Bonutti |
| 2004/0117018 A1 | 6/2004 | Michelson |
| 2004/0138689 A1 | 7/2004 | Bonutti |
| 2004/0138690 A1 | 7/2004 | Bonutti |
| 2004/0143270 A1 | 7/2004 | Zucherman et al. |
| 2004/0143285 A1 | 7/2004 | Bonutti |
| 2004/0143332 A1 | 7/2004 | Krueger et al. |
| 2004/0172033 A1 | 9/2004 | Bonutti |
| 2004/0176853 A1 | 9/2004 | Sennett et al. |
| 2004/0193181 A1 | 9/2004 | Bonutti |
| 2004/0230223 A1 | 11/2004 | Bonutti |
| 2005/0055098 A1 | 3/2005 | Zdeblick et al. |
| 2005/0065607 A1 | 3/2005 | Gross |
| 2005/0149192 A1 | 7/2005 | Zucherman et al. |
| 2005/0149193 A1 | 7/2005 | Zucherman et al. |
| 2005/0159819 A1 | 7/2005 | McCormack et al. |
| 2005/0171607 A1 | 8/2005 | Michelson |

(56) References Cited

U.S. PATENT DOCUMENTS

| | | |
|---|---|---|
| 2005/0177236 A1 | 8/2005 | Mathieu et al. |
| 2005/0187625 A1 | 8/2005 | Wolek et al. |
| 2005/0216059 A1 | 9/2005 | Bonutti |
| 2005/0240267 A1 | 10/2005 | Randall et al. |
| 2005/0240271 A1 | 10/2005 | Zubok et al. |
| 2005/0256574 A1 | 11/2005 | Paul et al. |
| 2005/0267534 A1 | 12/2005 | Bonutti |
| 2006/0085071 A1* | 4/2006 | Lechmann et al. ........ 623/17.11 |
| 2006/0129240 A1 | 6/2006 | Lessar et al. |
| 2006/0167495 A1 | 7/2006 | Bonutti |
| 2006/0217809 A1 | 9/2006 | Albert et al. |
| 2006/0235470 A1 | 10/2006 | Bonutti |
| 2006/0265009 A1 | 11/2006 | Bonutti |
| 2007/0088441 A1 | 4/2007 | Duggal et al. |
| 2007/0106388 A1 | 5/2007 | Michelson |
| 2007/0123987 A1 | 5/2007 | Bernstein |
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0208378 A1 | 9/2007 | Bonutti |
| 2007/0225806 A1 | 9/2007 | Squires et al. |
| 2007/0225810 A1 | 9/2007 | Colleran et al. |
| 2007/0225812 A1 | 9/2007 | Gill |
| 2007/0233253 A1 | 10/2007 | Bray et al. |
| 2007/0250167 A1 | 10/2007 | Bray et al. |
| 2007/0270961 A1 | 11/2007 | Ferguson |
| 2008/0039873 A1 | 2/2008 | Bonutti |
| 2008/0047567 A1 | 2/2008 | Bonutti |
| 2008/0051890 A1 | 2/2008 | Waugh et al. |
| 2008/0051907 A1 | 2/2008 | Marik |
| 2008/0058822 A1 | 3/2008 | Bonutti |
| 2008/0065140 A1 | 3/2008 | Bonutti |
| 2008/0103519 A1 | 5/2008 | Bonutti |
| 2008/0108916 A1 | 5/2008 | Bonutti |
| 2008/0114399 A1 | 5/2008 | Bonutti |
| 2008/0133013 A1 | 6/2008 | Duggal et al. |
| 2008/0140116 A1 | 6/2008 | Bonutti |
| 2008/0140117 A1 | 6/2008 | Bonutti |
| 2009/0076608 A1 | 3/2009 | Gordon et al. |
| 2009/0210062 A1 | 8/2009 | Thalgott et al. |
| 2010/0057206 A1 | 3/2010 | Duffield |
| 2010/0145460 A1 | 6/2010 | Mcdonough |
| 2010/0305704 A1* | 12/2010 | Messerli et al. ........... 623/17.16 |
| 2011/0087327 A1 | 4/2011 | Lechmann |
| 2011/0166658 A1 | 7/2011 | Garber et al. |
| 2011/0251689 A1 | 10/2011 | Seifert |
| 2012/0010623 A1 | 1/2012 | Bonutti |
| 2012/0215226 A1 | 8/2012 | Bonutti |
| 2012/0215233 A1 | 8/2012 | Bonutti |
| 2012/0221017 A1 | 8/2012 | Bonutti |
| 2012/0245690 A1 | 9/2012 | Cowan, Jr. et al. |
| 2013/0110247 A1 | 5/2013 | Doran et al. |
| 2013/0226185 A1 | 8/2013 | Bonutti |
| 2013/0237989 A1 | 9/2013 | Bonutti |
| 2013/0289729 A1 | 10/2013 | Bonutti |
| 2014/0012380 A1 | 1/2014 | Laurence et al. |
| 2014/0018854 A1 | 1/2014 | Bonutti |
| 2014/0025110 A1 | 1/2014 | Bonutti |
| 2014/0025111 A1 | 1/2014 | Bonutti |
| 2014/0025112 A1 | 1/2014 | Bonutti |
| 2014/0039623 A1 | 2/2014 | Iott et al. |
| 2014/0228963 A1 | 8/2014 | Bonutti |
| 2014/0257380 A1 | 9/2014 | Bonutti |
| 2010/4030956 | 10/2014 | Bonutti |
| 2014/0343573 A1 | 11/2014 | Bonutti |

FOREIGN PATENT DOCUMENTS

| | | |
|---|---|---|
| WO | 9963914 A1 | 12/1999 |
| WO | 2005007040 A1 | 1/2005 |
| WO | 2007098288 A2 | 8/2007 |
| WO | 2008014258 A2 | 1/2008 |

OTHER PUBLICATIONS

U.S. Appl. No. 60/777,732, Feb. 27, 2006, Messerli et al.
U.S. Appl. No. 60/838,229, Aug. 16, 2006, Hunziker et al.
Guidance Document: Intervertebral Body Fusion Device, U.S. Dept. of Health and Human Services, Food and Drug Administration (Jun. 12, 2007).
M. Spruit et al., The in vitro stabilizing effect of polyetheretherketone cages versus a titanium cage of similar design for anterior lumbar interbody fusion, 14(8) Eur. Spine J. 752, 752-758 (2005).
P. Schleicher et al., Biomechanical comparison of two different concepts for stand alone anterior lumbar interbody fusion, 17(12) Eur. Spine J. 1757, 1757-1765 (2008).
P.W. Pavlov et al., Anterior lumbar interbody fusion with threaded fusion cages and autologous bone grafts, 9 Eur. Spine J. 224, 224-229 (2000).

* cited by examiner

INTERVERTEBRAL FUSION IMPLANT

CROSS-REFERENCE TO RELATED APPLICATIONS

The present application is a continuation of U.S. application Ser. No. 12/477,958 filed on Jun. 4, 2009, which is incorporated in its entirety herein.

FIELD OF THE INVENTION

The present disclosure generally relates to a fixation device for positioning and immobilizing at least two adjacent vertebra. In particular, the present invention relates to a stand alone interbody fusion device for implementation in the spine.

BACKGROUND OF THE INVENTION

The vertebrate spine is the axis of the skeleton on which all of the body parts "hang". In humans, the normal spine has seven cervical, twelve thoracic and five lumbar segments. The lumbar spine situs upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy.

However, the success or failure of spinal fusion may depend upon several factors. For instance the spacer or implant or cage used to fill the space left by the removed disc and bony anatomy must be sufficiently strong to support the spine under a wide range of loading conditions. The spacer should also be configured so that it likely to remain in place once it has been positioned in the spine by the surgeon. Additionally the material used for the spacer should be biocompatible material and should have a configured that promotes bony ingrowth.

In combination with spacers or cages, a plating system is used to further stabilize the spine during the fusion process. These devices, commonly referred to as bone fixation plating systems, typically include one or more plates and screws for aligning and holding vertebrae in a fixed position with respect to one another. Plating systems independent of the spacers provide additional complications such as loosening and failure of the hardware. Two common failures are the breakage of the plates, and the backing out of screws into soft tissues of the patient's body. The backing out of the screws is typically a result of the screws failure to achieve a sufficient purchase in the bone, although the stripping of the screws has also been known to cause this problem.

There is a need for a spine stabilization system that in promotes fusion of adjacent vertebrae while at the same time provides stabilization of the spinal area where fusion occurs. There is a need for a system that incorporates both the fusion element and the plating element in one system to reduce the possible complications that may occur. There is also a need to provide a system that reduces the complications that may occur in the fusion element and the plating element and to need for this system to be configured so that positioning this system is efficient and easy.

SUMMARY OF THE INVENTION

The present invention provides an intervertebral implant for implantation in a treated area of an intervertebral space between vertebral bodies of a spine. The implant includes a spacer portion having an inferior and superior surface, wherein the inferior and superior surfaces each have a contact area capable of engaging with anatomy in the treated area, and the inferior and superior surfaces define a throughhole extending through the spacer body. The present invention further provides screw holes extending from a side portion to the inferior and superior surfaces of the spacer portion and a plate portion coupled to the spacer portion through a coupling means, wherein the plate portion contains screws holes for receiving screws. A screw back out prevention mechanism adapted on the plate portion and prevents the back out of screws from the screw holes.

DETAILED DESCRIPTION OF THE ILLUSTRATED EMBODIMENTS

Figure 3:
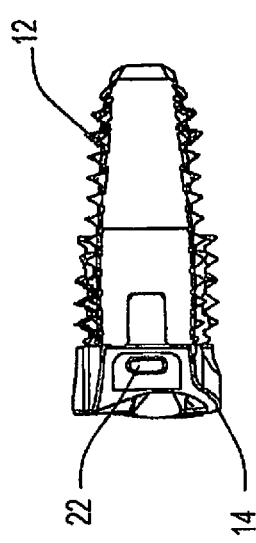
FIG. 3 is a side view of the intervertebral implant of FIG. 1.
Figure 4:
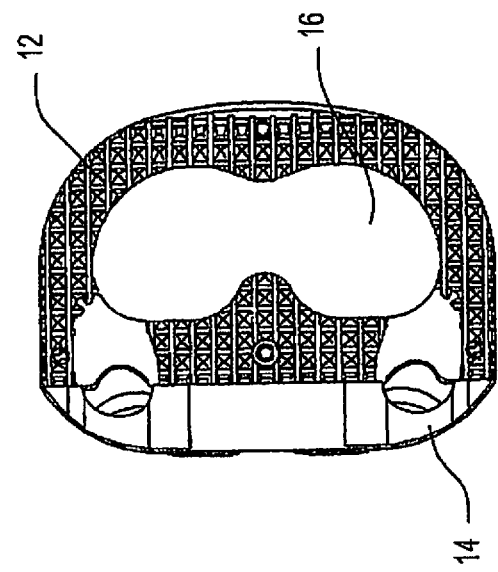
FIG. 4 is a top view of the intervertebral implant of FIG. 1.

Embodiments of the disclosure are generally directed to flexible stabilization systems for use with the anterior, antero-lateral, lateral, and/or posterior portions of at least one motion segment unit of the spine. The systems of the invention are designed to be conformable to the spinal anatomy, so as to be generally less intrusive to surrounding tissue and vasculature than existing rigid stabilization systems.

Certain embodiments may be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible area.

FIGS. 1-8 illustrate the different views of one particular embodiment of the present invention. The intervertebral fusion implant as shown in FIGS. 1-8 is a stand-alone anterior lumbar interbody fusion device used to provide structural stability in skeletally mature individuals following discectomies. These implants are available in various heights and geometric options to fit the anatomically needs of a wide variety of patients.

Specifically, FIGS. 1-4 illustrate one embodiment of an intervertebral fusion implant 10 according to the present invention. Implant 10 is generally positioned in the intervertebral space between two adjacent vertebrae. As shown in the figures, implant 10 primarily incorporates a spacer portion 12 and a plate portion 14. In this particular embodiment, the spacer portion 12 includes a graft window 16 for the placement of bone graft to enhance fusion between two adjacent vertebrae. The plate portion 14 includes at least one screw hole 18, however, in the preferred embodiment of the present invention, three screw holes 18 are provided. Also, in the plate portion 14 of the implant 10, a screw back out prevention mechanism 20 is provided. There is also provided a coupling means 22 which connect the spacer portion 12 and the plate portion 14 rigidly to each other. The coupling means 22 will be discussed in greater detail with reference to FIGS. 5-8.

The spacer portion 12 can be comprised of any material that is conducive to the enhancement of fusion between the two adjacent vertebrae. In one particular embodiment, the spacer portion 12 is made of PEEK material which is physiologically compatible. It should be noted that any other material that are physiologically compatible may also be used. The spacer portion 12 is made from radiolucent polymer in order to permit radiographic visualization. The spacer portion 12 further comprises superior and inferior portions that are provided with a plurality of pyramidal protrusions 13. The superior and inferior portions of the spacer portion are bi-convex for greater contact with the vertebral endplates of the adjacent vertebrae. The protrusions 13 can be configured to be any size or shape for further anchoring the spacer portion 12 to each of the adjacent vertebrae. Protrusions 13 on the superior and inferior surfaces of each implant grip the endplates of the adjacent vertebrae to aid in expulsion resistance.

Figure 1:
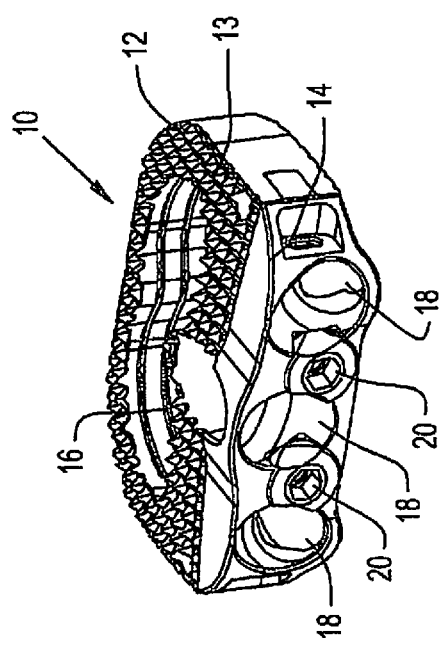
FIG. 1 is a perspective view of one embodiment of an intervertebral implant according to the present invention.
Figure 2:
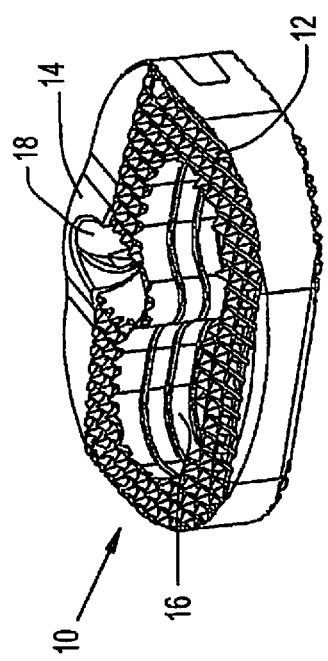
FIG. 2 is another perspective view of the embodiment of the implant shown in FIG. 1.

The plate portion 14 can also be comprised of any physiologically compatible material. In the preferred embodiment, the plate portion of the implant 10 is composed of titanium. The plate portion 14 as illustrated in FIG. 1, are provided with three screw holes. However, it should be noted that implant 10 may be comprised of only one screw hole. The screw holes 18 are situated both in the spacer portion 12 and the plate portion 14 for receiving bone screws which are attached to the adjacent vertebral bodies at different angles.

Figure 5:
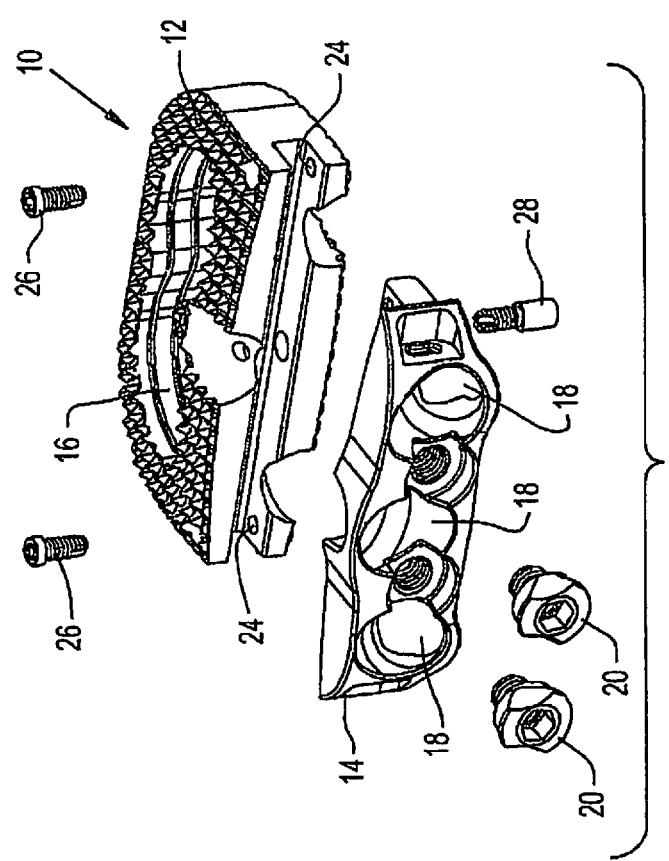
FIG. 5 is an exploded view of the intervertebral implant of FIG. 1.

FIG. 5 illustrates an exploded view of the intervertebral stand along fusion device 10. In this exploded view, clearer view of the combination of the plate portion 14 and the spacer portion 12 is illustrated. The spacer portion 12 and the plate portion 14 are coupled to each other view connection points 24 and through the use of connection pins 26 and 28.

Figure 6:
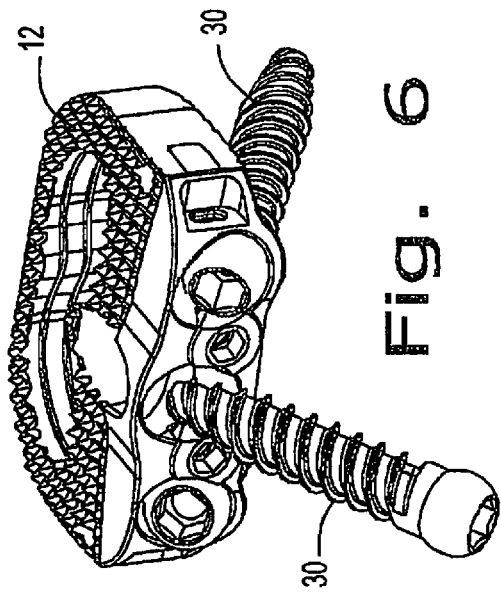
FIGS. 6 and 7 is a perspective view of the intervertebral implant of FIG. 1 which include illustrations of bone fasteners.
Figure 7:
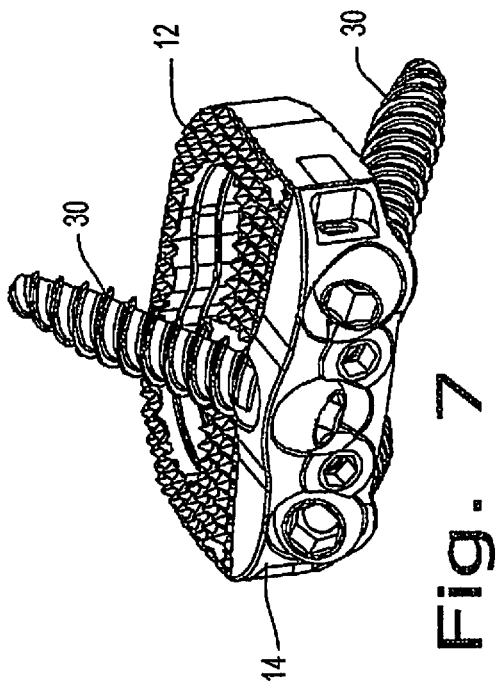
Figure 8:
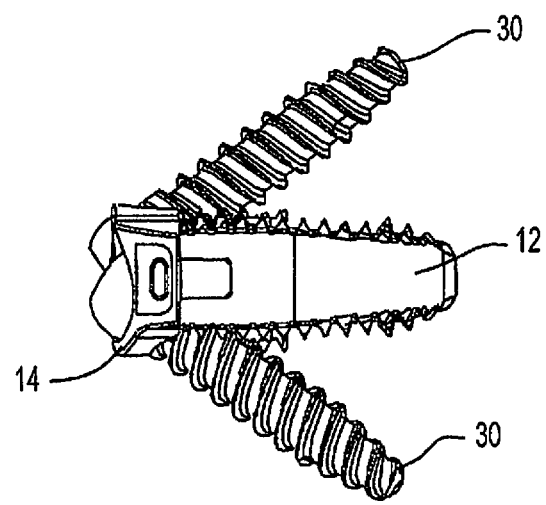
FIG. 8 is another side view of the intervertebral implant of FIG. 1 incorporating bone fasteners.

FIGS. 6-8 illustrate the fusion device 10 in various views associated with the screws 30 provided in pin holes 18. The pin holes 18 are configured to receive screws 30 at various angles. The screws 30 enter the pin holes at specified angles to enter the adjacent vertebral bodies at the optimal locations. The screws 30 are configured and adapted to provide optical purchase with the adjacent vertebral bodies.

Now, turning to the method of positioning the implant, it should be noted that the intervertebral implant 10 is positioned in the spine after the disc portion between two vertebral bodies is exposed and removed using rongeurs and other suitable instruments. The posterior and lateral walls of the annulus are generally preserved to provide peripheral support for the implant and graft materials. A trial device attached to a trial holder is then inserted into the disc space to determine size of the implant. This procedure is generally conducted using fluoroscopy and tactile feel. After the appropriate sized implant is selected and attached to an implant holder and drill guide, the implant may be inserted into the disc space. Once the implant is positioned with the disc space, supplemental graft material can used to enhance fusion. Once the implant is positioned inside the disc, an awl or any similar type of instrument can be used to drill through the screw hole and break the cortex of the adjacent vertebral body. The surgeon performing this procedure may then use a depth gauge to determine the screw length. Once the appropriate screw length is determined, screws are inserted using a self-retaining screwdriver. After the screws are finally inserted and secure thereby providing solid purchase with the adjacent vertebral bodies, the screw anti back out mechanism is engaged and secure. In this particular embodiment, the anti back out mechanism is two set screws that retain the three screws with the implant.

Figure 9:
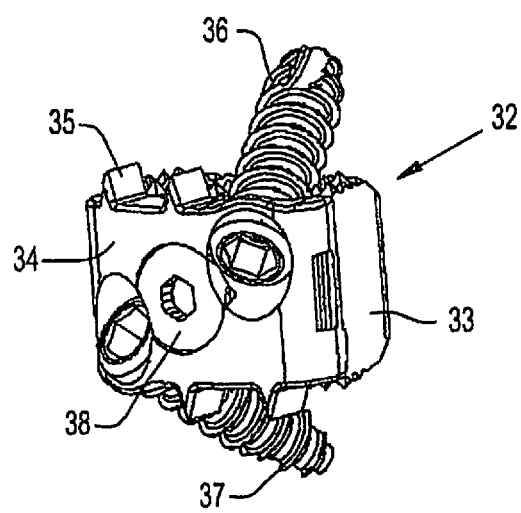
FIG. 9 is a perspective view of another embodiment of the stand alone intervertebral implant.

FIG. 9 illustrates a perspective view of the stand alone intervertebral implant 32 for positioning in the cervical region of the spine. The present invention relates to an implant having a peek spacer portion 33 that is coupled to a titanium plate portion 34 through the use of titanium dowel pins. However, it should be noted that the titanium plate portion 34 and the peek spacer portion 33 maybe coupled through any other feasible means such as hooks, screws, and any other type of fastening means. The implant 32 also allows for at least two titanium screws 36 and 37 to be inserted at a compound angle for maximum screw purchase into the superior and inferior vertebral bodies. A locking mechanism 38 is provided on the plate portion 34 to capture the sides of both of the at least two screws 36 and 37 with a 90 degree turn preventing the titanium screws 36 and 37 from backing out. It should be noted that the present application is not limited to being of a PEEK spacer and a titanium plate. Other materials that are physiologically compatible which are similar and which may be unique to spacers and plates may be utilized in various combinations.

Figure 10:
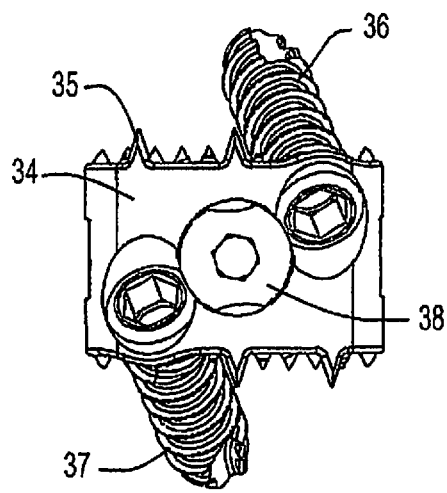
FIG. 10 is a front view of the intervertebral implant of FIG. 9.
Figure 11:
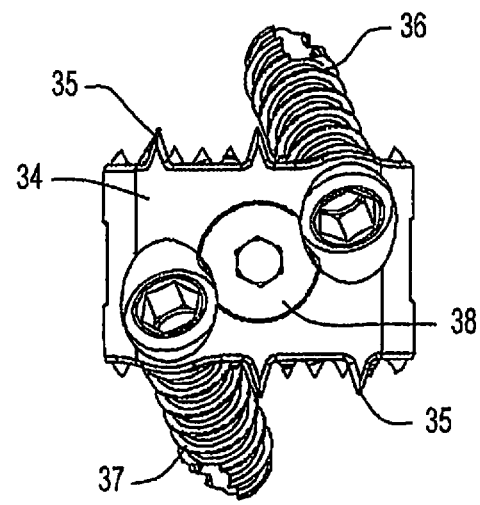
FIG. 11 is a top view of the stand alone intervertebral implant illustrated in FIG. 9.

FIGS. 10 and 11 illustrate the front view of the plate portion of the implant. Specifically, FIGS. 10 and 11 illustrate an open and a close position with reference to the anti back out mechanism 38. Also, it should be noted that the titanium plate 34 is provided with knife like edges 35 which are designed to engage the vertebral body and provides additional torsional stability to that of the bone screws. The plate 35 is also provided with "eye brows" like structure which fully captures the bone screws 36 and 37 while still allowing for the screws to reside about the tooth root plane and remaining lower than the tooth (protrusions on the spacer portion 33). The plate 35 geometry allows for the minimum reduction of peek volume. The plate 35 height remains level to the peek tooth root so that compressive loads are always subjected to the peek body where the graft is contained. Compound holes are drilled to accept bone screws 36 and 37 and to allow for fixed or variable angle screws. The anti back out mechanism is engaged so that the screws 26 and 37 do not back out of the implant 32.

Figure 12:
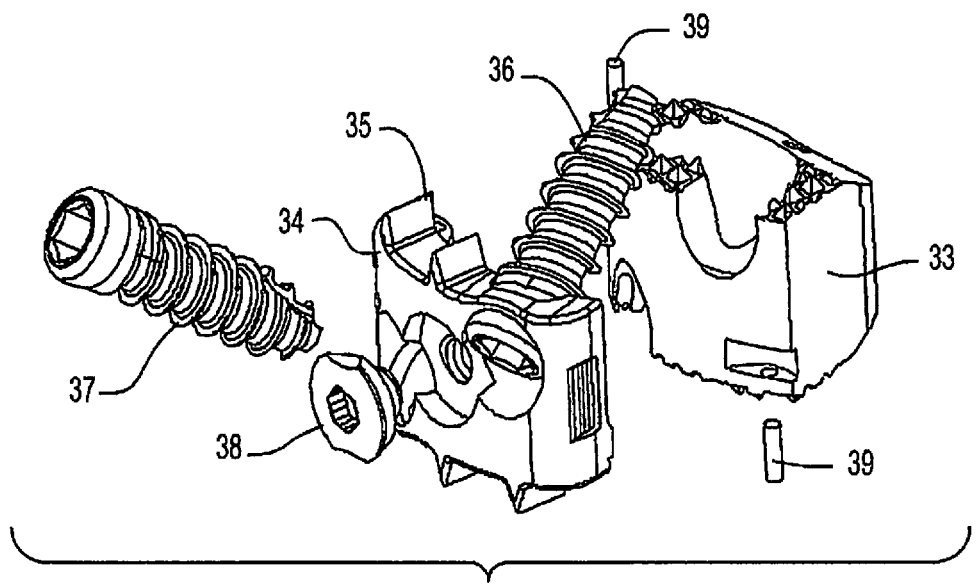
FIG. 12 is an exploded view of the stand alone intervertebral implant of FIG. 9.
Figure 14:
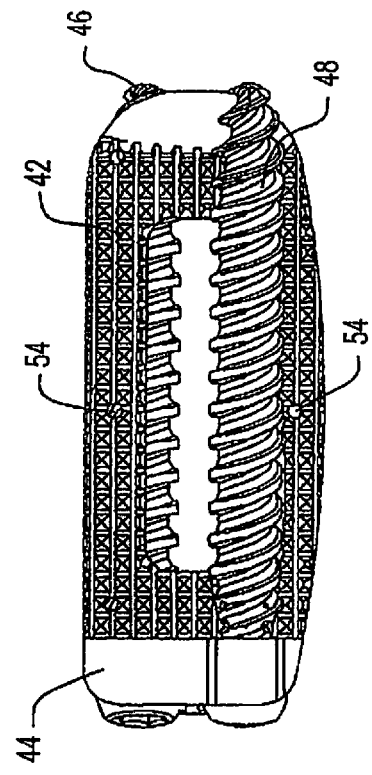
FIG. 14-16 are different views of the stand alone intervertebral implant of FIG. 13.
Figure 16:
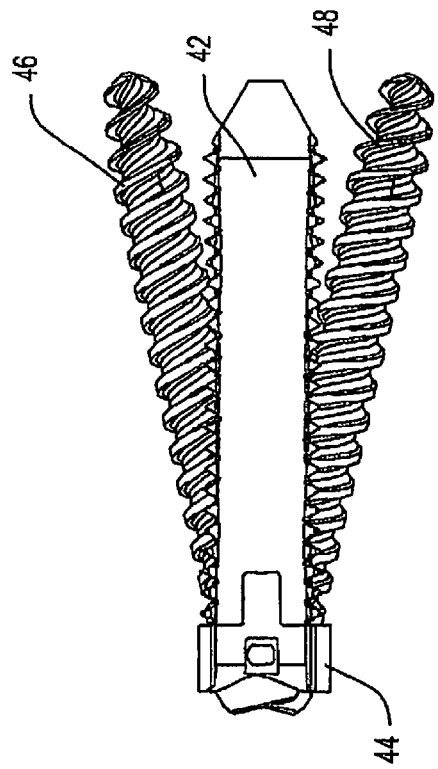
Figure 13:
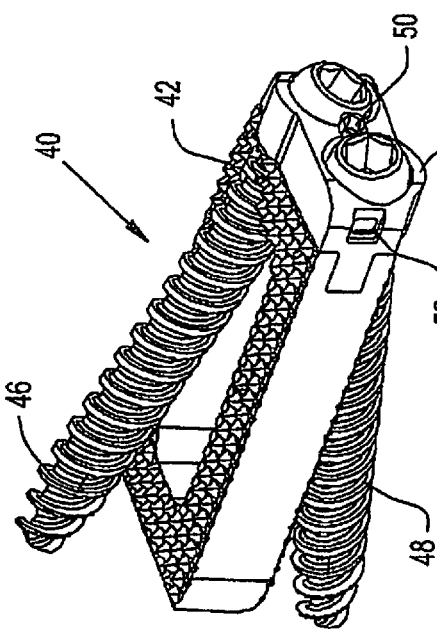
FIG. 13 is yet another embodiment of the stand alone intervertebral implant.
Figure 15:
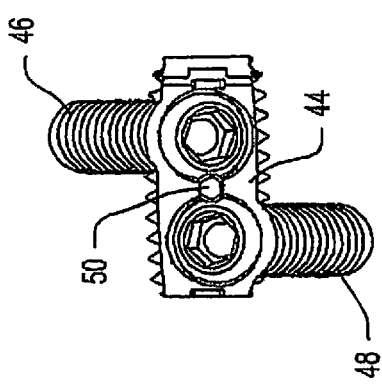

FIG. 12 illustrates an exploded view of the intervertebral implant. The plate portion 34 and spacer portion 33 have at least 2 male and female ledges which are capable of interfacing with each other. The connection of the male and female ledges are offset at different heights to minimize cross-sectional area loss. Also illustrated in FIG. 12 is the dowel pins used to connect the spacer portion to the plate portion as one means of coupling of the spacer portion 33 and the plate portion 34. It should be noted that various means such as hooks, staples and screws can be used to attach the spacer portion to the plate portion of the present invention.

The spacer portion 33 of the implant provides a leading edge chamfer which enables self distraction of the vertebral bodies while inserting. The spacer portion 33 also provides teeth like structures in the superior and inferior aspects of the spacer body to help prevent migration of the implant. The root of the teeth or protrusions on the base of the implant serves as the defining plane for the superior and inferior vertebral bodies. Finally, the spacer portion 33 provides an axial shaped hole which enables a maximum amount of graft for packing within the implant. However, it should be noted that the graft hole can be designed to be multiple holes or any in other geometrical shape to enhance fusion through the insertion of graft material.

FIGS. 13-16 illustrate a stand-alone fusion device for position in a lateral approach. The stand-alone fusion device 40 consists of a spacer portion 42 and a plate potion 44. The spacer portion and the plate portion are configured to be able to receive screws 46 and 48 for attachment to adjacent vertebral bodies. The plate portion 44 is provided with an anti back out mechanism 50 so that the screws 46 and 48 are fixedly retained within the fusion device 40.

Figure 17:
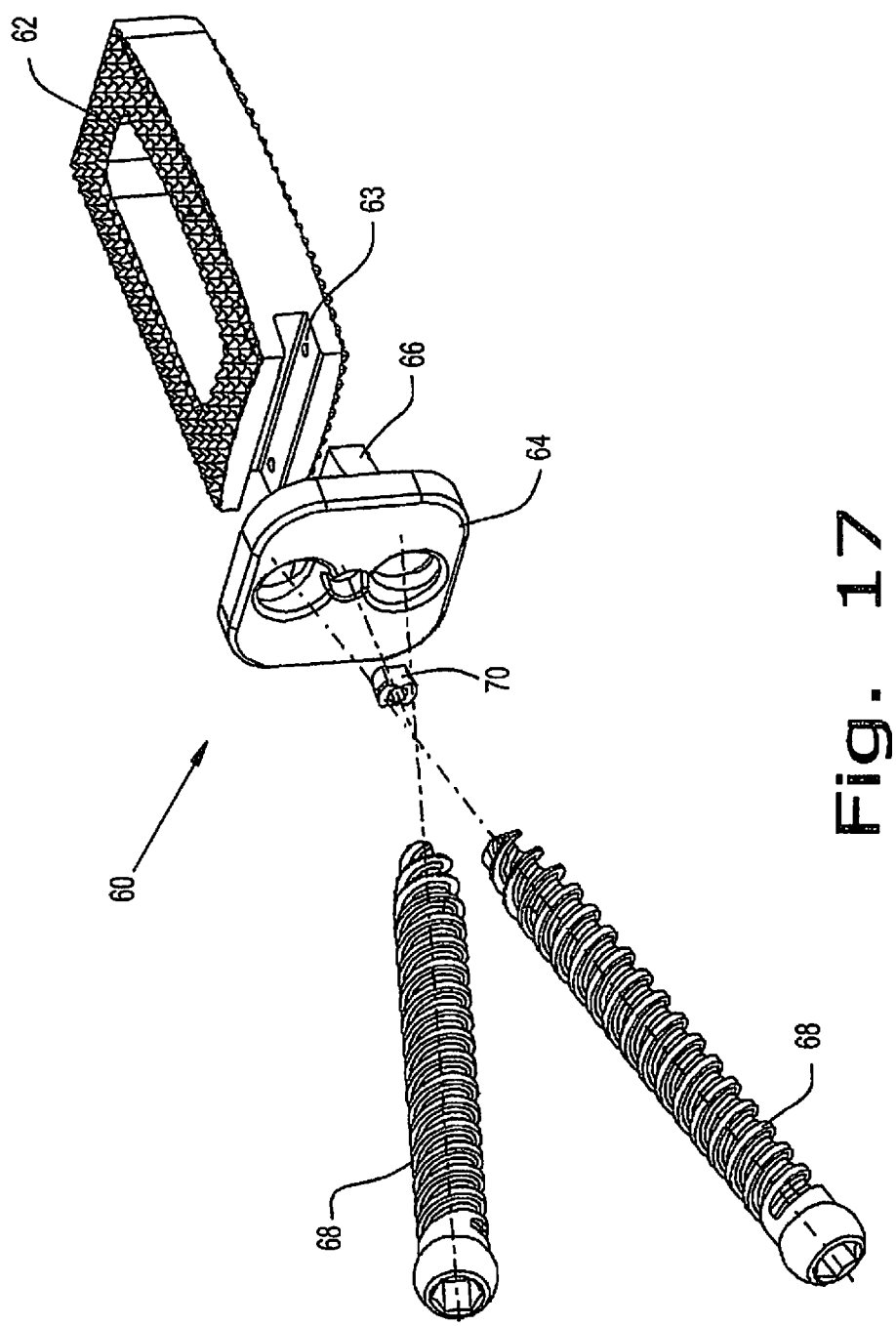
FIG. 17 is another embodiment of the implant of FIG. 14 according to the present invention.

FIG. 17 illustrates another embodiment of a stand-alone intervertebral implant 60 that is poisoned into the disc space laterally. In this embodiment, which is similar to the embodiment disclosed in FIGS. 13-16, the spacer portion 62 is provided with a plurality of protrusions in the superior and inferior portions. These protrusions grip the endplates of the adjacent vertebrae to aid in expulsion resistance. The spacer portion 62 also contains a plate receiving area 63 for receiving the plate portion 64. The plate receiving area 62 is configured to receive a plate protrusion 66 for coupling the spacer portion 62 and the plate portion 63 together through the use of pins or any other similar type of coupling means.

The plate portion 64 is configured with at least two screw holes for receiving screws 68. The screws 68 are positioned at angles to insert through the spacer and the adjacent vertebral body to gain maximum purchase and stability. The screws 68 are retained with the implant 60 through the use of an anti screw back out mechanism 70. When this mechanism is engaged by turning at least 90 degrees through the use an instrument such as a screwdriver, the screws 68 are maintained within the implant and the boney structure of the adjacent vertebral bodies.

While it is apparent that the invention disclosed herein is well calculated to fulfill the objects stated above, it will be appreciated that numerous modifications and embodiments may be devised by those skilled in the art.

What is claimed is:

1. An intervertebral implant for implantation in a treated area of an intervertebral space between vertebral bodies of a spine, wherein said implant comprises:
   a spacer having, an inferior and superior surface, wherein the inferior and superior surfaces each have a contact area capable of engaging with anatomy in the treated area, and the inferior and superior surfaces define a through-hole having an inner surface extending through the spacer;
   through holes extending from a side portion to the inferior and superior surfaces of the spacer;
   a plate rigidly coupled to the spacer, wherein the plate contains through holes for receiving fasteners; and
   wherein a fastener back out prevention mechanism is adapted on the plate for preventing the back out of screws from the screw holes,
   wherein the plate comprises an extension that is adapted to mate with a connection groove on an anterior portion of the spacer, wherein the connection groove in the spacer includes a first vertical opening for receiving a first connection pin therethrough and a second vertical opening for receiving a second connection pin therethrough to thereby secure the plate to the spacer,
   wherein the fastener back out prevention mechanism includes a rotatable element that in a first position allows for at least two fasteners to be inserted or removed from through holes of the plate and when rotated into a second position secures the at least two fasteners within the intervertebral implant,
   and wherein the plate is not moveable with respect to the spacer.

2. The intervertebral implant of claim 1, wherein the at least two fasteners are configured to be inserted into adjacent vertebral bodies at divergent angles.

3. The intervertebral implant of claim 1, wherein at least one pin rigidly couples the spacer with the plate.

4. The intervertebral implant of claim 1, wherein the plate and the spacer are configured to structurally mate with one another.

5. The intervertebral implant of claim 1, wherein the plate is comprised of metal.

6. The intervertebral implant of claim 1, wherein at least one groove is configured circumferentially on the inner surface of the spacer.

7. The intervertebral implant of claim 1, wherein the spacer is comprised of plastic.

8. The intervertebral implant of claim 1, wherein the spacer comprises a plurality of protrusions on superior and inferior surfaces of the spacer.

9. An intervertebral implant for implantation in a treated area of an intervertebral space between vertebral bodies of a spine, wherein said implant comprises:
   a spacer having an inferior and superior surface, wherein the inferior and superior surfaces each have a contact area capable of engaging with anatomy in the treated area, and the inferior and superior surfaces define a through-hole and an inner surface extending through the spacer;

screw holes extending to the inferior and superior surfaces of the spacer;

a plate rigidly coupled to the spacer, wherein the plate contains screws holes for receiving screws; and a screw back out prevention mechanism adapted on the plate and prevents the back out of screws from the screw holes, wherein the plate comprises an extension that is adapted to mate with a connection groove on an anterior portion of the spacer, the extension extending an entire length of the plate and the connection groove extending the entire length of the anterior portion of the spacer, wherein the connection groove in the spacer includes a first vertical opening for receiving a first connection pin therethrough and a second vertical opening for receiving a second connection pin therethrough to thereby secure the plate to the spacer, wherein the fastener back out prevention mechanism includes a rotatable element that in a first position allows for at least two fasteners to be inserted or removed from through holes of the plate and when rotated into a second position secures the at least two fasteners within the intervertebral implant, and wherein the plate is not moveable with respect to the spacer.

10. The intervertebral implant of claim 9, wherein the at least two fasteners are configured to be inserted into adjacent vertebral bodies at divergent angles.

11. The intervertebral implant of claim 10, wherein the spacer comprises a plurality of protrusions on the superior and inferior surfaces of the spacer.

12. The intervertebral implant of claim 9, wherein at least one pin couples the spacer portion and the plate of the intervertebral implant.

13. The intervertebral implant of claim 9, wherein the plate and the spacer are configured to structurally mate with one another.

14. The intervertebral implant of claim 9, wherein the plate is comprised of metal and the spacer is comprised of plastic.

15. An implant for positioning between adjacent intervertebral bodies comprising:

a spacer having an anterior portion, a posterior portion, first and second side portions, and superior and inferior surfaces; and a plate having an anterior face and a posterior face, first and second side portions, and superior and inferior surfaces wherein the plate comprises an extension extending out from a posterior portion of the plate and extending an entire length of the plate, wherein the extension of the plate mates with a connection groove of the spacer, the connection groove of the spacer configured on the anterior portion of the spacer and extending an entire length of the spacer, wherein the connection groove in the spacer includes a first vertical opening for receiving a first connection pin therethrough and a second vertical opening for receiving a second connection pin therethrough to thereby secure the plate to the spacer, where connection pins couple the spacer to the plate so that the plate does not move with respect to the spacer, wherein the fastener back out prevention mechanism includes a rotatable element that in a first position allows for at least two fasteners to be inserted or removed from through holes of the plate and when rotated into a second position secures the at least two fasteners within the intervertebral implant.

* * * * *